United States Patent
Hays et al.

(10) Patent No.: US 7,981,995 B2
(45) Date of Patent: Jul. 19, 2011

(54) SILICONE POLYOXAMIDE AND SILICONE POLYOXAMIDE-HYDRAZIDE COPOLYMERS

(75) Inventors: David S. Hays, Woodbury, MN (US); Richard G. Hansen, Mahtomedi, MN (US); Stephen A. Johnson, Woodbury, MN (US); Benjamin J. Bending, Madison, WI (US); Kyle J. Lindstrom, Houlton, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 12/563,311

(22) Filed: Sep. 21, 2009

(65) Prior Publication Data

US 2011/0071270 A1     Mar. 24, 2011

(51) Int. Cl.
C08G 77/06     (2006.01)

(52) U.S. Cl. .................................................. 528/26

(58) Field of Classification Search .................. 528/26
See application file for complete search history.

(56) References Cited

U.S. PATENT DOCUMENTS

| | | |
|---|---|---|
| 2,676,182 A | 4/1954 | Daudt et al. |
| 3,627,851 A | 12/1971 | Brady |
| 3,772,247 A | 11/1973 | Flannigan |
| 3,890,269 A | 6/1975 | Martin |
| 4,661,577 A | 4/1987 | Jo Lane et al. |
| 4,935,484 A | 6/1990 | Wolfgruber et al. |
| 5,026,890 A | 6/1991 | Webb et al. |
| 5,082,706 A | 1/1992 | Tangney |
| 5,214,119 A | 5/1993 | Leir et al. |
| 5,248,739 A | 9/1993 | Schmidt et al. |
| 5,276,122 A | 1/1994 | Aoki et al. |
| 5,302,685 A | 4/1994 | Tsumura et al. |
| 5,319,040 A | 6/1994 | Wengrovius et al. |
| 5,461,134 A | 10/1995 | Leir et al. |
| 5,512,650 A | 4/1996 | Leir et al. |
| 5,670,598 A | 9/1997 | Leir et al. |
| 6,355,759 B1 | 3/2002 | Sherman et al. |
| 6,531,620 B2 | 3/2003 | Brader et al. |
| 7,371,464 B2 | 5/2008 | Sherman et al. |
| 7,501,184 B2 * | 3/2009 | Leir et al. ............... 428/448 |
| 2003/0175510 A1 | 9/2003 | Sherman et al. |
| 2007/0148474 A1 * | 6/2007 | Leir et al. ............... 428/447 |
| 2007/0177272 A1 | 8/2007 | Benson et al. |
| 2009/0099291 A1 | 4/2009 | Jia et al. |

OTHER PUBLICATIONS

"Silicones", Encyclopedia of Polymer Science and Engineering, vol. 15, John Wiley & Sons, New York (1989) pp. 265-270.

* cited by examiner

*Primary Examiner* — Margaret G Moore
(74) *Attorney, Agent, or Firm* — Lisa P. Fulton; James A. Baker

(57) ABSTRACT

Silicone polyoxamide and silicone polyoxamide-hydrazide copolymers comprise at least two repeating units of formula I

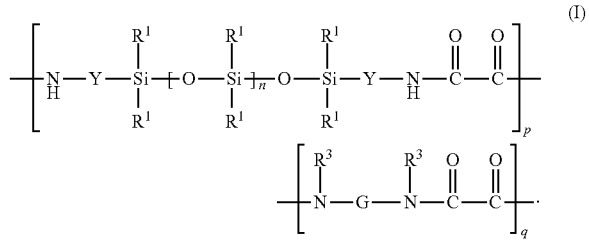

In this formula, each $R^1$ is independently an alkyl, haloalkyl, aralkyl, alkenyl, aryl, or aryl substituted with an alkyl, alkoxy, or halo; each Y is independently an alkylene, aralkylene, or a combination thereof; each G is independently a bond or a divalent residue equal to a diamine of formula $R^3HN$-G-$NHR^3$ minus the two —$NHR^3$ groups; each $R^3$ is independently hydrogen or alkyl or $R^3$ taken together with G and with the nitrogen to which they are both attached form a heterocyclic group; each n is independently an integer of 0 to 1500; each p is independently an integer of 1 to 10, and the average of p is 1.2 or greater; and each q is independently an integer of 1 or greater, and every q is not the same integer.

18 Claims, No Drawings

SILICONE POLYOXAMIDE AND SILICONE POLYOXAMIDE-HYDRAZIDE COPOLYMERS

FIELD

This invention relates to silicone polyoxamide and silicone polyoxamide-hydrazide copolymers and to methods of making the copolymers.

BACKGROUND

Siloxane polymers have unique properties derived mainly from the physical and chemical characteristics of the siloxane bond. These properties include low glass transition temperature, thermal and oxidative stability, resistance to ultraviolet radiation, low surface energy and hydrophobicity, high permeability to many gases, and biocompatibility. The siloxane polymers, however, often lack tensile strength.

The low tensile strength of the siloxane polymers can be improved by forming block copolymers. Some block copolymers contain a "soft" siloxane polymeric block or segment and any of a variety of "hard" blocks or segments. Polydiorganosiloxane polyamides, polydiorganosiloxane polyureas, and polydiorganosiloxane polyoxamide copolymers are exemplary block copolymers.

Polydiorganosiloxane polyamides have been prepared by condensation reactions of amino terminated silicones with short-chained dicarboxylic acids. Alternatively, these copolymers have been prepared by condensation reactions of carboxy terminated silicones with short-chained diamines. Because polydiorganosiloxanes (e.g., polydimethylsiloxanes) and polyamides often have significantly different solubility parameters, it can be difficult to find reaction conditions for production of siloxane-based polyamides that result in high degrees of polymerization, particularly with larger homologs of the polyorganosiloxane segments. Many of the known siloxane-based polyamide copolymers contain relatively short segments of the polydiorganosiloxane (e.g., polydimethylsiloxane) such as segments having no greater than 30 diorganosiloxy (e.g., dimethylsiloxy) units or the amount of the polydiorganosiloxane segment in the copolymer is relatively low. That is, the fraction (i.e., amount based on weight) of polydiorganosiloxane (e.g., polydimethylsiloxane) soft segments in the resulting copolymers tends to be low.

Polydiorganosiloxane polyureas are another type of block copolymer. Although these block copolymers have many desirable characteristics, some of them tend to degrade when subjected to elevated temperatures such as 250° C. or higher.

Polydiorganosiloxane polyoxamides such as those disclosed in U.S. Pat. No. 7,501,184 (Leir et al.) are yet another type of block copolymer. Known polydiorganosiloxane polyoxamide copolymers have been made by mixing a diamine such as ethylene diamine with a precursor that includes at least one polydiorganosiloxane segment and at least two oxalylamino groups. The resulting copolymers have alternating soft polydiorganosiloxane segments (S) and hard oxamide segments (H) (i.e., the copolymers are of a $(S-H)_n$ type). These polydiorganosiloxane polyoxamide copolymers thus contain a relatively large fraction of the polydiorganosiloxane segment compared to many known polydiorganosiloxane polyamide copolymers. Such polydiorganosiloxane polyoxamide copolymers can usually be subjected to elevated temperatures up to 250° C. or higher without apparent degradation.

SUMMARY

In view of the foregoing, we recognize that although the alternating soft and hard segment polydiorganosiloxane polyamide copolymers described above are an improvement over less thermally stable thermoplastic silicone elastomers, it would be advantageous to have the ability to control the level and distribution of hard segments within the copolymer chain.

Briefly, in one aspect, the present invention provides silicone polyoxamide and silicone polyoxamide-hydrazide copolymers comprising at least two repeating units of formula I:

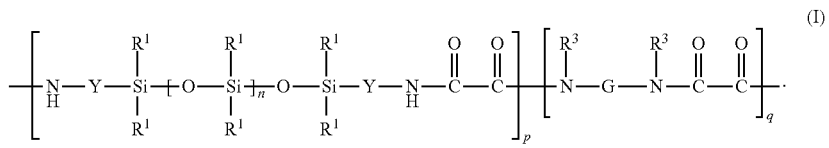

In this formula, each $R^1$ is independently an alkyl, haloalkyl, aralkyl, alkenyl, aryl, or aryl substituted with an alkyl, alkoxy, or halo; each Y is independently an alkylene, aralkylene, or a combination thereof; each G is independently a bond or a divalent residue equal to a diamine of formula $R^3HN$-G-$NHR^3$ minus the two —$NHR^3$ groups; each $R^3$ is independently hydrogen or alkyl or $R^3$ taken together with G and with the nitrogen to which they are both attached form a heterocyclic group; each n is independently an integer of 0 to 1500; each p is independently an integer of 1 to 10, and the average of p is 1.2 or greater; and each q is independently an integer of 1 or greater, and every q is not the same integer.

The silicone polyoxamide and silicone polyoxamide-hydrazide copolymers of the invention can have random "runs" of hard segments, where q is 2 or greater, and need not have perfectly alternating soft and hard segments. Properties such as solvent resistance, modulus, hardness, melt rheology, shear, and/or adhesion can be improved by the incorporation of hard segment runs in the copolymers.

In another aspect, the present invention provides a method of making a copolymeric material comprising at least two repeat units of formula I':

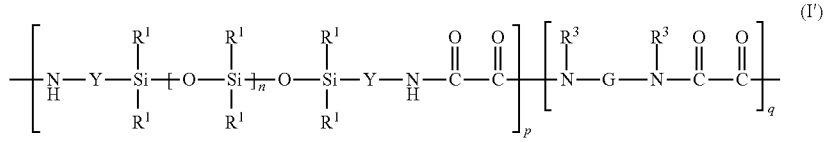

wherein $R^1$, Y, G, $R^3$, n, p, and q are defined as above, and every q is not the same, but the average of p may be less than 1.2.

The method comprises (a) adding an oxalate ester of formula II to a solvent

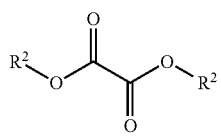
(II)

wherein each $R^2$ is independently an alkyl, haloalkyl, aryl, or aryl substituted with an alkyl, alkoxy, halo, alkyoxycarbonyl, or

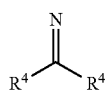

bound through the N, wherein each $R^4$ is independently hydrogen, alkyl, or aryl or $R^4$ taken together form a ring; (b) reacting a molar excess of the oxalate ester with a polydiorganosiloxane diamine of formula III until essentially no polydiorganosiloxane diamine remains

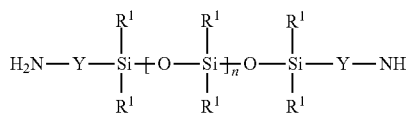
(III)

to form the reaction product of formula IV

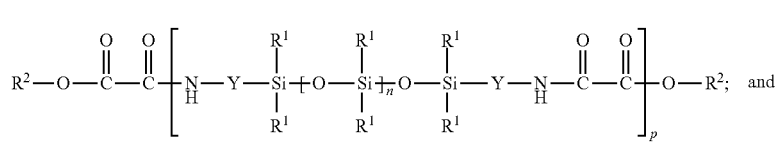
(IV)

(c) adding one or more diamines of formula V to the reaction product of formula IV to form the repeat unit of formula I'

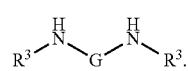
(V)

Previously known methods of making polydiorganosiloxane polyoxamide copolymers such as the method disclosed in U.S. Pat. No. 7,501,184 (Leir et al.) result in only (S—H)$_n$ type copolymers. The method of the invention, however, can be used to make copolymers having runs of hard segments.

In yet another aspect the present invention provides a novel compound having the following formula:

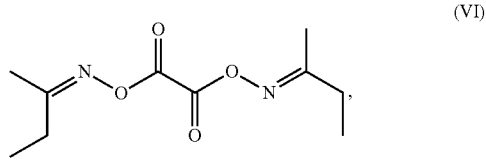
(VI)

and geometric isomers thereof.

The compound of formula VI is useful in the method of the invention for making a copolymeric material comprising at least two repeat units of formula I'. Furthermore, this compound possesses the following desirable properties. It is highly reactive (e.g., it is more reactive than conventional oxalate esters such diethyl oxalate). Its by-product (i.e., methyl ethyl ketone oxime) is a volatile liquid, and its starting materials are relatively inexpensive and readily available.

DETAILED DESCRIPTION

The silicone polyoxamide and silicone polyoxamide-hydrazide copolymers of the invention comprise at least two repeating units of formula I:

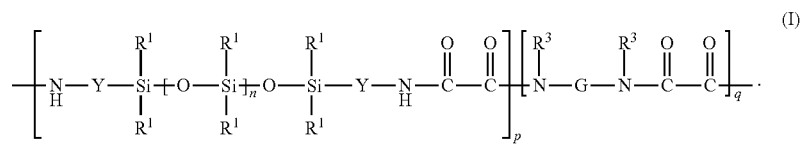
(I)

In this formula, each $R^1$ is independently an alkyl, haloalkyl, aralkyl, alkenyl, aryl, or aryl substituted with an alkyl, alkoxy, or halo; each Y is independently an alkylene, aralkylene, or a combination thereof; each G is independently a bond or a divalent residue equal to a diamine of formula $R^3$HN-G-NHR$^3$ minus the two —NHR$^3$ groups; each $R^3$ is independently hydrogen or alkyl or $R^3$ taken together with G and with the nitrogen to which they are both attached form a heterocyclic group (e.g., $R^3$HN-G-NHR$^3$ is piperazine or the like); each n is independently an integer of 0 to 1500; each p is independently an integer of 1 to 10, and the average of p is 1.2 or greater; and each q is independently an integer of 1 or greater, and every q is not the same integer.

Suitable alkyl groups for $R^1$ in formula I typically have 1 to 10, 1 to 6, or 1 to 4 carbon atoms. Exemplary alkyl groups include, but are not limited to, methyl, ethyl, isopropyl, n-propyl, n-butyl, and iso-butyl. Suitable haloalkyl groups for $R^1$ often have only a portion of the hydrogen atoms of the corresponding alkyl group replaced with a halogen. Exemplary haloalkyl groups include chloroalkyl and fluoroalkyl groups with 1 to 3 halo atoms and 3 to 10 carbon atoms. Suitable alkenyl groups for $R^1$ often have 2 to 10 carbon atoms. Exemplary alkenyl groups often have 2 to 8, 2 to 6, or 2 to 4 carbon atoms such as ethenyl, n-propenyl, and n-butenyl. Suitable aryl groups for $R^1$ often have 6 to 12 carbon atoms. Phenyl is an exemplary aryl group. The aryl group can be unsubstituted or substituted with an alkyl (e.g., an alkyl having 1 to 10 carbon atoms, 1 to 6 carbon atoms, or 1 to 4 carbon atoms), an alkoxy (e.g., an alkoxy having 1 to 10 carbon atoms, 1 to 6 carbon atoms, or 1 to 4 carbon atoms), or halo (e.g., chloro, bromo, or fluoro). Suitable aralkyl groups for $R^1$ usually have an alkylene group with 1 to 10 carbon atoms and an aryl group with 6 to 12 carbon atoms. In some exemplary aralkyl groups, the aryl group is phenyl and the alkylene group has 1 to 10 carbon atoms, 1 to 6 carbon atoms, or 1 to 4 carbon atoms (i.e., the structure of the aralkyl is alkylene-phenyl where an alkylene is bonded to a phenyl group).

In some embodiments, in some repeat units of formula I, at least 40 percent, and preferably at least 50 percent, of the $R^1$ groups are methyl. For example, at least 60 percent, at least 70 percent, at least 80 percent, at least 90 percent, at least 95 percent, at least 98 percent, or at least 99 percent of the $R^1$ groups can be methyl. The remaining $R^1$ groups can be selected from an alkyl having at least two carbon atoms, haloalkyl, aralkyl, alkenyl, aryl, or aryl substituted with an alkyl, alkoxy, or halo.

Each Y in formula I is independently an alkylene, aralkylene, or a combination thereof Suitable alkylene groups typically have up to 10 carbon atoms, up to 8 carbon atoms, up to 6 carbon atoms, or up to 4 carbon atoms. Exemplary alkylene groups include methylene, ethylene, propylene, butylene, and the like. Suitable aralkylene groups usually have an arylene group with 6 to 12 carbon atoms bonded to an alkylene group with 1 to 10 carbon atoms. In some exemplary aralkylene groups, the arylene portion is phenylene. That is, the divalent aralkylene group is phenylene-alkylene where the phenylene is bonded to an alkylene having 1 to 10, 1 to 8, 1 to 6, or 1 to 4 carbon atoms. As used herein with reference to group Y, "a combination thereof" refers to a combination of two or more groups selected from an alkylene and aralkylene group. A combination can be, for example, a single aralkylene bonded to a single alkylene (e.g., alkylene-arylene-alkylene). In one exemplary alkylene-arylene-alkylene combination, the arylene is phenylene and each alkylene has 1 to 10, 1 to 6, or 1 to 4 carbon atoms.

Each G in formula I is independently a bond or a residual unit that is equal to a diamine compound of formula $R^3$HN-G-NHR$^3$ minus the two amino groups (i.e., —NHR$^3$ groups). When G is a bond, the copolymer is a silicone polyoxamide-hydrazide. In some embodiments, G is a bond and each $R^3$ is hydrogen.

When G is a residual unit, the copolymer is a silicone polyoxamide. The diamine can have primary or secondary amino groups. Group $R^3$ is hydrogen or alkyl (e.g., an alkyl having 1 to 10, 1 to 6, or 1 to 4 carbon atoms) or $R^3$ taken together with G and with the nitrogen to which they are both attached forms a heterocyclic group (e.g., $R^3$HN-G-NHR$^3$ is piperazine). In most embodiments, $R^3$ is hydrogen or an alkyl. In many embodiments, both of the amino groups of the diamine are primary amino groups (i.e., both $R^3$ groups are hydrogen) and the diamine is of formula $H_2N$-G-$NH_2$.

In some embodiments, G is an alkylene, heteroalkylene, arylene, aralkylene, or a combination thereof Suitable alkylenes often have 2 to 10, 2 to 6, or 2 to 4 carbon atoms. Exemplary alkylene groups include ethylene, propylene, butylene, and the like. Suitable heteroalkylenes are often polyoxyalkylenes such as polyoxyethylene having at least 2 ethylene units, polyoxypropylene having at least 2 propylene units, or copolymers thereof. Suitable aralkylene groups usually contain an arylene group having 6 to 12 carbon atoms bonded to an alkylene group having 1 to 10 carbon atoms. Some exemplary aralkylene groups are phenylene-alkylene where the phenylene is bonded to an alkylene having 1 to 10 carbon atoms, 1 to 8 carbon atoms, 1 to 6 carbon atoms, or 1 to 4 carbon atoms. As used herein with reference to group G, "a combination thereof" refers to a combination of two or more groups selected from an alkylene, heteroalkylene, arylene, and aralkylene. A combination can be, for example, an aralkylene bonded to an alkylene (e.g., alkylene-arylene-alkylene). In one exemplary alkylene-arylene-alkylene combination, the arylene is phenylene and each alkylene has 1 to 10, 1 to 6, or 1 to 4 carbon atoms.

Each subscript n in formula I is independently an integer of 0 to 1500. For example, subscript n can be an integer up to 1000, up to 500, up to 400, up to 300, up to 200, up to 100, up to 80, up to 60, up to 40, up to 20, or up to 10. The value of n is often at least 1, at least 2, at least 3, at least 5, at least 10, at least 20, or at least 40. For example, subscript n can be in the range of 40 to 1500, 0 to 1000, 40 to 1000, 0 to 500, 1 to 500, 40 to 500, 1 to 400, 1 to 300, 1 to 200, 1 to 100, 1 to 80, 1 to 40, or 1 to 20.

Each subscript p is independently an integer of 1 to 10. For example, the value of p is often an integer up to 9, up to 8, up to 7, up to 6, up to 5, up to 4, up to 3, or up to 2. The value of p can be in the range of 1 to 8, 1 to 6, or 1 to 4. The average of p is 1.2 or greater.

Each subscript q is independently an integer of 1 or greater, and every q is not the same integer. In some embodiments, each subscript q is an integer of 1 to 10.

The copolymers of the invention tend to be free of groups having a formula —$R^a$—(CO)—NH— where $R^a$ is an alkylene. All of the carbonylamino groups along the backbone of the copolymeric material are part of an oxalylamino group (i.e., the —(CO)—(CO)—NH— group). That is, any carbonyl group along the backbone of the copolymeric material is bonded to another carbonyl group and is part of an oxalyl group. More specifically, the copolymers of the invention have a plurality of aminoxalylamino groups.

The silicone polyoxamide and silicone polyoxamide-hydrazide copolymers of the invention are linear block copolymers (i.e., they comprise hard blocks and soft blocks) and can be elastomeric. They tend to have better solvent resistance than previously known polydiorganosiloxane polyoxamides. Some of the copolymers of the invention are insoluble, for example, in toluene or even in tetrahydrofuran. For the purposes of this invention, the following method shall determine whether a copolymer is "insoluble" in a particular solvent. About 1 g of sample copolymer is placed in jar, approximately 100 g of the desired solvent is added, and the jar is sealed and placed on a roller at ambient temperature for approximately 4 hours. A copolymer sample is considered to be insoluble if, after drying to constant weight, ≧90% of the original mass is retained.

The copolymers of the invention also tend to have improved heat stability. Some of the copolymers of the invention, for example, do not flow at or below about 220° C., at or below about 260° C., or even at or below about 300° C. For the purposes of this invention, the temperature at which a copolymer flows is defined as the temperature at which the copolymer is sufficiently soft such that it compresses to a thickness of 2 mm in an ARES parallel plate rheometer (available from TA Instruments, New Castle, Del.).

The copolymers of the invention can be optically clear. As used herein, the term "optically clear" refers to a material that is clear to the human eye. An optically clear copolymeric material often has a luminous transmission of at least 90 percent, a haze of less than 2 percent, and opacity of less than 1 percent in the 400 to 700 nm wavelength range. Both the luminous transmission and the haze can be determined using, for example, the method of ASTM-D 1003-95.

Additionally, the copolymers can have a low refractive index. As used herein, the term "refractive index" refers to the absolute refractive index of a material (e.g., copolymeric material) and is the ratio of the speed of electromagnetic radiation in free space to the speed of the electromagnetic radiation in the material of interest. The electromagnetic radiation is white light. The index of refraction is measured using an Abbe refractometer, available commercially, for example, from Fisher Instruments of Pittsburgh, Pa. The measurement of the refractive index can depend, to some extent, on the particular refractometer used. The copolymeric material usually has a refractive index in the range of 1.41 to 1.50.

Functional components, tackifiers, plasticizers, and other property modifiers may be incorporated in the copolymer of the invention. Preferred optional additives are not hot melt processable. That is, they do not melt and flow at the temperatures at which the copolymer of the invention melts and flows.

Functional components include, for example, antistatic additives, ultraviolet light absorbers (UVAs), hindered amine light stabilizers (HALS), dyes, colorants, pigments, antioxidants, slip agents, low adhesion materials, conductive materials, abrasion resistant materials, optical elements, dimensional stabilizers, adhesives, tackifiers, flame retardants, phosphorescent materials, fluorescent materials, nanoparticles, anti-graffiti agents, dew-resistant agents, load bearing agents, silicate resins, fumed silica, glass beads, glass bubbles, glass fibers, mineral fibers, clay particles, organic fibers, e.g., nylon, KEVLAR, metal particles, and the like. Such optional additives can be added in amounts up to 100 parts per 100 parts of the copolymer of the invention, provided that if and when incorporated, such additives are not detrimental to the function and functionality of the final polymer product. Other additives such as light diffusing materials, light absorptive materials and optical brighteners, flame retardants, stabilizers, antioxidants, compatibilizers, antimicrobial agents such as zinc oxide, electrical conductors, thermal conductors such as aluminum oxide, boron nitride, aluminum nitride, and nickel particles, including organic and/or inorganic particles, or any number or combination thereof, can be blended into these systems. The functional components listed above may also be incorporated into copolymer of the invention provided such incorporation does not adversely affect the resulting product to an undesirable extent.

Tackifying materials or plasticizers useful with the polymeric materials are preferably miscible at the molecular level, e.g., soluble in, any or all of the polymeric segments of the elastomeric material or the thermoplastic elastomeric material. When the tackifying material is present it generally comprises 5 to 300 parts by weight, more typically up to 200 parts by weight, based on 100 parts by weight of the polymeric material. Examples of tackifiers suitable for the invention include but are not limited to silicone fluids, liquid rubbers, hydrocarbon resins, rosin, natural resins such as dimerized or hydrogenated balsams and esterified abietic acids, polyterpenes, terpene phenolics, phenol-formaldehyde resins, and rosin esters. Examples of plasticizers include but are not limited to polybutene, paraffinic oils, petrolatum, and certain phthalates with long aliphatic side chains such as ditridecyl phthalate.

Other suitable tackifiers include silicate tackifying resins. Suitable silicate tackifying resins include those resins composed of the following structural units M (i.e., monovalent $R_3SiO_{1/2}$ units), D (i.e., divalent $R_2SiO_{2/2}$ units), T (i.e., trivalent $RSiO_{3/2}$ units), and Q (i.e., quaternary $SiO_{4/2}$ units), and combinations thereof. Typical exemplary silicate resins include MQ silicate tackifying resins, MQD silicate tackifying resins, and MQT silicate tackifying resins. These silicate tackifying resins usually have a number average molecular weight in the range of 100 to 50,000 or in the range of 500 to 15,000 and generally have methyl R groups.

MQ silicate tackifying resins are copolymeric resins having $R_3SiO_{1/2}$ units ("M" units) and $SiO_{4/2}$ units ("Q" units), where the M units are bonded to the Q units, each of which is bonded to at least one other Q unit. Some of the $SiO_{4/2}$ units ("Q" units) are bonded to hydroxyl radicals resulting in $HOSiO_{3/2}$ units ("TOH" units), thereby accounting for the silicon-bonded hydroxyl content of the silicate tackifying resin, and some are bonded only to other $SiO_{4/2}$ units.

Such resins are described in, for example, Encyclopedia of Polymer Science and Engineering, vol. 15, John Wiley & Sons, New York, (1989), pp. 265-270, and U.S. Pat. No. 2,676,182 (Daudt et al.), U.S. Pat. No. 3,627,851 (Brady), U.S. Pat. No. 3,772,247 (Flannigan), and U.S. Pat. No. 5,248,739 (Schmidt et al.). Other examples are disclosed in U.S. Pat. No. 5,082,706 (Tangney). The above-described resins are generally prepared in solvent. Dried or solventless, M silicone tackifying resins can be prepared, as described in U.S. Pat. No. 5,319,040 (Wengrovius et al.), U.S. Pat. No. 5,302,685 (Tsumura et al.), and U.S. Pat. No. 4,935,484 (Wolfgruber et al.).

Certain MQ silicate tackifying resins can be prepared by the silica hydrosol capping process described in U.S. Pat. No. 2,676,182 (Daudt et al.) as modified according to U.S. Pat. No. 3,627,851 (Brady), and U.S. Pat. No. 3,772,247 (Flannigan). These modified processes often include limiting the concentration of the sodium silicate solution, and/or the silicon-to-sodium ratio in the sodium silicate, and/or the time before capping the neutralized sodium silicate solution to generally lower values than those disclosed by Daudt et al. The neutralized silica hydrosol is often stabilized with an alcohol, such as 2-propanol, and capped with $R_3SiO_{1/2}$ siloxane units as soon as possible after being neutralized. The level of silicon bonded hydroxyl groups (i.e., silanol) on the MQ resin may be reduced to no greater than 1.5 weight percent, no greater than 1.2 weight percent, no greater than 1.0 weight percent, or no greater than 0.8 weight percent based on the weight of the silicate tackifying resin. This may be accomplished, for example, by reacting hexamethyldisilazane with the silicate tackifying resin. Such a reaction may be catalyzed, for example, with trifluoroacetic acid. Alternatively, trimethylchlorosilane or trimethylsilylacetamide may be reacted with the silicate tackifying resin, a catalyst not being necessary in this case.

MQD silicone tackifying resins are terpolymers having $R_3SiO_{1/2}$ units ("M" units), $SiO_{4/2}$ units ("Q" units), and $R_2SiO_{2/2}$ units ("D" units) such as are taught in U.S. Pat. No. 2,736,721 (Dexter). In MQD silicone tackifying resins, some of the methyl R groups of the $R_2SiO_{2/2}$ units ("D" units) can be replaced with vinyl ($CH_2=CH-$) groups ("DVi" units).

MQT silicate tackifying resins are terpolymers having $R_3SiO_{1/2}$ units, $SiO_{4/2}$ units and $RSiO_{3/2}$ units ("T" units) such as are taught in U.S. Pat. No. 5,110,890 (Butler) and Japanese Kokai HE 2-36234.

Suitable silicate tackifying resins are commercially available from sources such as Dow Corning, Midland, Mich.; Momentive Performance Materials, Albany, N.Y.; and Rhodia Silicones, Rock Hill, S.C. Examples of particularly useful MQ silicate tackifying resins include those available under the trade designations SR-545 and SR-1000, both of which are commercially available from Momentive Performance Materials, Albany, N.Y. Such resins are generally supplied in organic solvent and may be employed in the formulations of the adhesives of the present invention as received. Blends of two or more silicate resins can be included in the adhesive compositions.

The copolymers of the invention can be cast from solvents or cast and polymerized as film, molded or embossed in various shapes, or extruded into films. The high temperature stability of the copolymeric material makes them well suited for extrusion methods of film formation. The films can be optically clear. A multilayer film containing polydiorganosiloxane polyoxamide block copolymers is described, for example, in U.S. Pat. No. 7,820,297 (Benson et al.).

The copolymers of the invention are useful in various articles. The articles, for example, can include a layer containing the copolymer of the invention and one or more optional substrates. For example, the copolymer of the invention can be in a layer adjacent to a first substrate or positioned between a first substrate and a second substrate. That is, the article can be arranged in the following order: a first substrate, a layer containing the copolymer of the invention, and a second substrate. As used herein, the term "adjacent" refers to a first layer that contacts a second layer or that is positioned in proximity to the second layer but separated from the second layer by one or more additional layers.

The copolymers of the invention can be formulated into adhesive compositions such as pressure sensitive adhesives and heat activated adhesives that contain a tackifier. Such adhesive compositions are further described, for example, in U.S. Pat. No. 7,371,464 (Sherman et al.).

Additionally, the copolymers of the invention can be used as a hot melt adhesive. Typically, the hot melt adhesive contains little or no tackifier. The hot melt adhesives can be used, for example, to bond two surfaces together into a composite. That is, the hot melt adhesive can be used to bond a first substrate to a second substrate with the hot melt adhesive positioned between the first and second substrates. During application to a surface such as the surface of a substrate, hot melt adhesives are desirably sufficiently fluid to wet the surface completely and leave no voids, even if the surface is rough. Such an adhesive composition typically has a low viscosity at the time of application and then sets into a solid upon cooling. The cohesive strength develops upon cooling. Alternatively, the hot melt adhesive composition can be formulated with a solvent or carrier that lowers the viscosity sufficiently to permit wetting of the surface. The solvent or carrier can then be removed to provide a solid coating having cohesive strength.

The copolymers of the invention are also useful as low adhesion backsize coatings.

The silicone polyoxamide and silicone polyoxamide-hydrazide copolymers of the invention (and other silicone polyoxamide and silicone polyoxamide-hydrazide copolymers) can be prepared according the method of the invention. The following method can be used to make a copolymeric material comprising at least two repeat units of formula I':

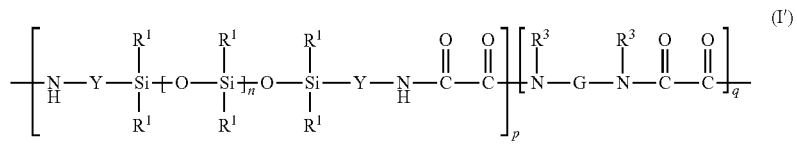

wherein each $R^1$ is independently an alkyl, haloalkyl, aralkyl, alkenyl, aryl, or aryl substituted with an alkyl, alkoxy, or halo; each Y is independently an alkylene, aralkylene, or a combination thereof; each G is independently a bond or a divalent residue equal to a diamine of formula $R^3HN\text{-}G\text{-}NHR^3$ minus the two $—NHR^3$ groups; each $R^3$ is independently hydrogen or alkyl or $R^3$ taken together with G and with the nitrogen to which they are both attached form a heterocyclic group; each n is independently an integer of 0 to 1500; each p is independently an integer of 1 to 10; and each q is independently an integer of 1 or greater, and every q is not the same integer.

Suitable examples of $R^1$, Y, G, and $R^3$ are the same as described above for formula I.

The first step of the method of the invention comprises adding an oxalate ester of formula II to a solvent

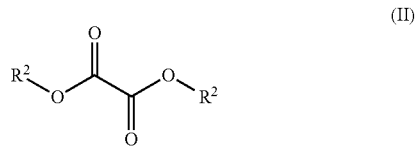

wherein each $R^2$ is independently an alkyl, haloalkyl, aryl, or aryl substituted with an alkyl, alkoxy, halo, alkyoxycarbonyl, or

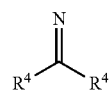

bound through the N, wherein each $R^4$ is independently hydrogen, alkyl, or aryl or $R^4$ taken together form a ring.

The two $R^2$ groups in the oxalate of formula II can be the same or different. In some methods, the two $R^2$ groups are different and have different reactivity with the polydiorganosiloxane diamine of formula III below.

Suitable alkyl and haloalkyl groups for $R^2$ often have 1 to 10, 1 to 6, or 1 to 4 carbon atoms. Although tertiary alkyl (e.g., tert-butyl) and haloalkyl groups can be used, there is often a primary or secondary carbon atom attached directly (i.e., bonded) to the adjacent oxy group. Exemplary alkyl groups include methyl, ethyl, n-propyl, iso-propyl, n-butyl, and iso-butyl. Exemplary haloalkyl groups include chloroalkyl groups and fluoroalkyl groups in which some, but not all, of the hydrogen atoms on the corresponding alkyl group are replaced with halo atoms. For example, the chloroalkyl or a fluoroalkyl groups can be chloromethyl, 2-chloroethyl, 2,2,2-trichloroethyl, 3-chloropropyl, 4-chlorobutyl, fluoromethyl, 2-fluoroethyl, 2,2,2-trifluoroethyl, 3-fluoropropyl, 4-fluorobutyl, and the like. Suitable aryl groups for $R^2$ include those having 6 to 12 carbon atoms such as, for example, phenyl. An aryl group can be unsubstituted or substituted with an alkyl (e.g., an alkyl having 1 to 4 carbon atoms such as methyl, ethyl, or n-propyl), an alkoxy (e.g., an alkoxy having 1 to 4 carbon atoms such as methoxy, ethoxy, or propoxy), halo (e.g., chloro, bromo, or fluoro), or alkoxycarbonyl (e.g., an alkoxycarbonyl having 2 to 5 carbon atoms such as methoxycarbonyl, ethoxycarbonyl, or propoxycarbonyl).

The oxalates of formula II can be prepared, for example, by reaction of an alcohol of formula R²—OH with oxalyl dichloride. Commercially available oxalates of formula II (e.g., from Sigma-Aldrich, Milwaukee, Wis. and from VWR International, Bristol, Conn.) include, but are not limited to, dimethyl oxalate, diethyl oxalate, di-n-butyl oxalate, di-tert-butyl oxalate, bis(phenyl)oxalate, bis(pentafluorophenyl)oxalate, 1-(2,6-difluorophenyl)-2-(2,3,4,5,6-pentachlorophenyl)oxalate, and bis (2,4,6-trichlorophenyl)oxalate.

Particularly useful oxalate esters of formula II include, for example, oxalate esters of phenol, methyl ethyl ketone oxime, acetone oxime, and trifluoroethanol.

Suitable solvents include, for example, tetrahydrofuran, methyl tert-butyl ether, toluene, ethyl acetate, dichloromethane, chloroform and the like, or any solvent that does not interfere with the desired reaction.

After the oxalate ester has been added to the solvent, polydiorganosiloxane diamine of formula III is added and reacted with a molar excess of the oxalate

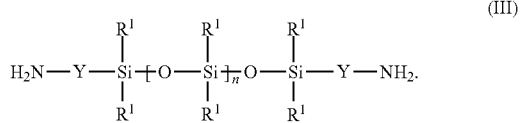
(III)

This reaction is typically done under an inert atmosphere.

The polydiorganosiloxane diamine of formula III can be prepared by any known method and can have any suitable molecular weight, such as an average molecular weight in the range of 700 to 150,000 g/mole. In some preferred embodiments, the polydiorganosiloxane diamine of formula III has a number average molecular weight of about 1000 g/mol to about 50,000 g/mol. Suitable polydiorganosiloxane diamines and methods of making the polydiorganosiloxane diamines are described, for example, in U.S. Pat. No. 3,890,269 (Martin), U.S. Pat. No. 4,661,577 (Jo Lane et al.), U.S. Pat. No. 5,026,890 (Webb et al.), U.S. Pat. No. 5,276,122 (Aoki et al.), U.S. Pat. No. 5,214,119 (Leir et al.), U.S. Pat. No. 5,461,134 (Leir et al.), U.S. Pat. No. 5,512,650 (Leir et al.), and U.S. Pat. No. 6,355,759 (Sherman et al.), incorporated herein by reference in their entirety. Some polydiorganosiloxane diamines are commercially available, for example, from Shin Etsu Silicones of America, Inc., Torrance, Calif. and from Gelest Inc., Morrisville, Pa.

A polydiorganosiloxane diamine having a molecular weight greater than 2,000 g/mole or greater than 5,000 g/mole can be prepared using the methods described in U.S. Pat. No. 5,214,119 (Leir et al.), U.S. Pat. No. 5,461,134 (Leir et al.), and U.S. Pat. No. 5,512,650 (Leir et al.). One of the described methods involves combining under reaction conditions and under an inert atmosphere (a) an amine functional end blocker of the following formula

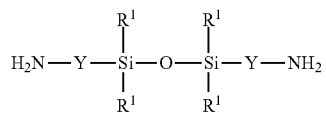

where Y and R¹ are the same as defined for formula I'; (b) sufficient cyclic siloxane to react with the amine functional end blocker to form a polydiorganosiloxane diamine having a molecular weight less than 2,000 g/mole; and (c) an anhydrous aminoalkyl silanolate catalyst of the following formula

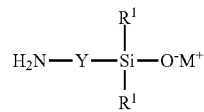

where Y and R¹ are the same as defined in formula I' and M⁺ is a sodium ion, potassium ion, cesium ion, rubidium ion, or tetramethylammonium ion. The reaction is continued until substantially all of the amine functional end blocker is consumed and then additional cyclic siloxane is added to increase the molecular weight. The additional cyclic siloxane is often added slowly (e.g., drop wise). The reaction temperature is often conducted in the range of 80° C. to 90° C. with a reaction time of 5 to 7 hours. The resulting polydiorganosiloxane diamine can be of high purity (e.g., less than 2 weight percent, less than 1.5 weight percent, less than 1 weight percent, less than 0.5 weight percent, less than 0.1 weight percent, less than 0.05 weight percent, or less than 0.01 weight percent silanol impurities). Altering the ratio of the amine end functional blocker to the cyclic siloxane can be used to vary the molecular weight of the resulting polydiorganosiloxane diamine of formula III.

Another method of preparing the polydiorganosiloxane diamine of formula III includes combining under reaction conditions and under an inert environment (a) an amine functional end blocker of the following formula

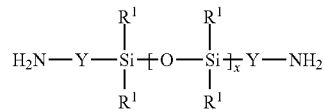

where R¹ and Y are the same as described for formula I' and where the subscript x is equal to an integer of 1 to 150; (b) sufficient cyclic siloxane to obtain a polydiorganosiloxane diamine having an average molecular weight greater than the average molecular weight of the amine functional end blocker; and (c) a catalyst selected from cesium hydroxide, cesium silanolate, rubidium silanolate, cesium polysiloxanolate, rubidium polysiloxanolate, and mixtures thereof. The reaction is continued until substantially all of the amine functional end blocker is consumed. This method is further described in U.S. Pat. No. 6,355,759 B1 (Sherman et al.). This procedure can be used to prepare any molecular weight of the polydiorganosiloxane diamine.

Yet another method of preparing the polydiorganosiloxane diamine of formula III is described in U.S. Pat. No. 6,531,620 B2 (Brader et al.). In this method, a cyclic silazane is reacted with a siloxane material having hydroxy end groups as shown in the following reaction.

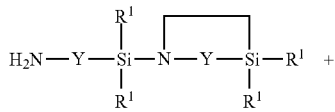

-continued

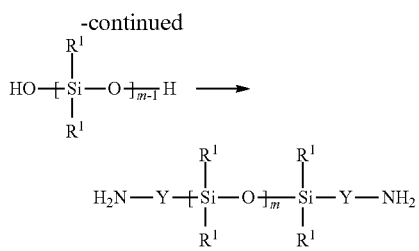

The groups $R^1$ and Y are the same as described for formula I'. The subscript m is an integer greater than 1.

Examples of polydiorganosiloxane diamines include, but are not limited to, polydimethylsiloxane diamine, polydiphenylsiloxane diamine, polytrifluoropropylmethylsiloxane diamine, polyphenylmethylsiloxane diamine, polydiethylsiloxane diamine, polydivinylsiloxane diamine, polyvinylmethylsiloxane diamine, poly(5-hexenyl)methylsiloxane diamine, and mixtures thereof.

The mixture of oxalate ester and polydiorganosiloxane diamine is allowed to react until essentially no polydiorganosiloxane diamine remains as measured, for example, by titration. The resulting reaction product of formula IV is formed

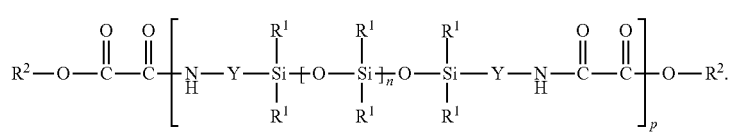

The resulting reaction mixture contains some ester-capped polydiorganosiloxane diamine in which p is dependent upon the amount of oxalate ester utilized and on the nature of the solvent utilized. The reaction mixture also contains some unreacted oxalate ester of formula II. The remaining oxalate ester enables runs of hard segments of random lengths (e.g., q greater than or equal 2 in the repeat unit of formula I') to be produced in the following step.

Next, one or more diamines of formula V are added to the reaction product of formula IV to form the repeat unit of formula I'

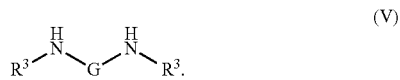

The diamine is typically added in a quantity to consume the remaining ester groups.

The diamines of formula V are sometimes classified as organic diamines. Organic diamines include, for example, those selected from alkylene diamines, heteroalkylene diamines, arylene diamines, aralkylene diamines, or alkylene-aralkylene diamines. The diamine has only two amino groups so that the resulting polydiorganosiloxane polyoxamides and polyoxamide-hydrazides are linear block copolymers that are often elastomeric, molten at elevated temperatures, and soluble in some common organic solvents. The diamine is free of a polyamine having more than two primary or secondary amino groups. Tertiary amines that do not react with the reaction product of formula IV can be present. Additionally, the diamine is free of any carbonylamino group. That is, the diamine is not an amide.

Exemplary polyoxyalkylene diamines (i.e., G is a heteroalkylene with the heteroatom being oxygen) include, but are not limited to, those commercially available from Huntsman, The Woodlands, Tex. under the trade designation JEFFAMINE D-230 (i.e., polyoxypropropylene diamine having an average molecular weight of 230 g/mole), JEFFAMINE D-400 (i.e., polyoxypropylene diamine having an average molecular weight of 400 g/mole), JEFFAMINE D-2000 (i.e., polyoxypropylene diamine having an average molecular weight of 2,000 g/mole), JEFFAMINE HK-511 (i.e., polyetherdiamine with both oxyethylene and oxypropylene groups and having an average molecular weight of 220 g/mole), JEFFAMINE ED-2003 (i.e., polypropylene oxide capped polyethylene glycol having an average molecular weight of 2,000 g/mole), and JEFFAMINE EDR-148 (i.e., triethyleneglycol diamine).

Exemplary alkylene diamines (i.e., G is a alkylene) include, but are not limited to, ethylene diamine, propylene diamine, butylene diamine, hexamethylene diamine, 2-methylpentamethylene 1,5-diamine (i.e., commercially available from DuPont, Wilmington, Del. under the trade designation DYTEK A), 1,3-pentane diamine (commercially available from DuPont under the trade designation DYTEK EP), 1,4-cyclohexane diamine, 1,2-cyclohexane diamine (commercially available from DuPont under the trade designation DHC-99), 4,4'-bis(aminocyclohexyl)methane, and 3-aminomethyl-3,5,5-trimethylcyclohexylamine.

Exemplary arylene diamines (i.e., G is an arylene such as phenylene) include, but are not limited to, m-phenylene diamine, o-phenylene diamine, and p-phenylene diamine. Exemplary aralkylene diamines (i.e., G is an aralkylene such as alkylene-phenyl) include, but are not limited to 4-aminomethyl-phenylamine, 3-aminomethyl-phenylamine, and 2-aminomethyl-phenylamine. Exemplary alkylene-aralkylene diamines (i.e., G is an alkylene-aralkylene such as alkylene-phenylene-alkylene) include, but are not limited to, 4-aminomethyl-benzylamine, 3-aminomethyl-benzylamine, and 2-aminomethyl-benzylamine.

Exemplary hydrazines (i.e., G is a bond) include, but are not limited to, hydrazine and N,N'-diaminopiperazine.

In some preferred embodiments, the diamine of formula V is selected from the group consisting of 1,2-diaminoethane, 1,3-diaminopropane, 1,4-diaminobutane, 1,5-diaminopentane, 2-methyl-1,5-pentanediamine, 1,6-diaminohexane, and m-xylylenediamine.

Any suitable reactor (e.g., a glass vessel or a standard kettle equipped with agitators) or process can be used to prepare the copolymeric material according to the method of the invention. The reaction can be conducted using a batch process, semi-batch process, or a continuous process.

EXAMPLES

Objects and advantages of this invention are further illustrated by the following examples, but the particular materials and amounts thereof recited in these examples, as well as other conditions and details, should not be construed to unduly limit this invention. All parts, percentages, ratios, and the like in the examples and are by weight, unless noted otherwise. Solvents and other reagents used were obtained from Sigma-Aldrich Chemical Company, Milwaukee, Wis. or EMD Chemicals, Gibbstown, N.J. unless otherwise noted.

| Table of Materials | |
|---|---|
| Component | Description |
| PDMS diamine | A polydimethylsiloxane diamine of the following formula<br><br>$H_2N-\diagup\diagdown-Si(CH_3)_2-[O-Si(CH_3)_2]_n-O-Si(CH_3)_2-\diagup\diagdown-NH_2$<br><br>with a number average molecular weight of about 25,000 g/mole (25 k) or 33,000 g/mole (33 k) prepared according to U.S. Pat. No. 5,214,119. Unstripped PDMS diamine contains about 13 percent by weight of volatile cyclics as described in U.S. Pat. No. 5,026,890. |
| IPA | 2-propanol, EMD Chemicals, Gibbstown, NJ |
| MTBE | tert-butyl methyl ether, EMD Chemicals, Gibbstown, NJ |
| MIBK | 4-methyl-2-pentanone, EMD Chemicals, Gibbstown, NJ |
| bis(2,2,2-trifluoroethyl) oxalate | prepared according to US2007149745 |
| MQ resin | Dow Corning 2-7066, Dow Corning Midland, MI |
| DYTEK A | 2-methyl-1,5-pentanediamine, Dupont, Wilmington, DE |
| XTJ-582 | poly(oxy(methyl-1,2-ethanediyl)),alpha-(2-aminomethylethyl)omega-(2-aminomethylethoxy), Huntsman, The Woodlands, TX |
| $D_4$ | Octamethylcyclotetrasiloxane, Gelest Inc, Morrisville, PA |
| octaphenyl $D_4$ | Octaphenylcyclotetrasiloxane, Gelest Inc, Morrisville, PA |
| N,N'-diaminopiperazine | prepared according to Sorenson, W. R.; Sweeny, F.; Campbell, T. W. Preparative Methods of Polymer Chemistry; Wiley: New York, 2001; p 96. |

Test Methods
Titration Method to Determine Amine Equivalent Weight (AEW) of PDMS Diamines The amine equivalent weight (AEW) of PDMS diamines were determined in tetrahydrofuran (THF) using standardized HCL (1N) and titrating against a bromophenol blue endpoint.

Inherent Viscosity (IV)

Average inherent viscosities (IV) were measured at 27° C. using a Canon-Fenske viscometer (Model No. 50 P296) in a THF solution at 27° C. at a concentration of 0.2 g/dL. The inherent viscosities were averaged over 3 or more runs. Any variations for determining average inherent viscosities are set forth in specific Examples. The values are reported in dL/g.

180° Peel Strength

This peel adhesion test is similar to the test method described in ASTM D 3330-90, substituting a glass substrate, polymethylmethacrylate substrate, or polycarbonate substrate for the stainless steel substrate described in the test.

Unless otherwise noted, adhesive coatings on primed PET (HOSTAPHAN 3SAB primed polyester film available from Mitsubishi Polyester Film Inc, Greer, S.C.) were cut into 1.27 centimeter by 15 centimeters strips. Each strip was then adhered to a 10 centimeters by 20 centimeters clean, solvent washed, glass coupon using a 2-kilogram roller passed once over the strip. The bonded assembly dwelled at room temperature for about one minute and was tested for 180° peel adhesion using an IMASS slip/peel tester (Model 3M90, commercially available from Instrumentors Inc., Strongsville, Ohio) at a rate of 2.3 meters/minute (90 inches/minute) over a five second data collection time. Two samples were tested; the reported peel adhesion value was an average of the peel adhesion value from each of the two samples. Peel adhesion values were recorded in ounces/inch and converted to Newtons/decimeter (N/dm).

Shear Strength

This shear strength test is similar to the test method described in ASTM D 3654-88. Unless otherwise noted, adhesive coatings on polyester film were cut into 1.27 centimeter (0.5 inch) by 15 centimeters (6 inch) strips. Each strip was then adhered to a stainless steel panel such that a 1.27 centimeters by 1.27 centimeter portion of each strip was in firm contact with the panel and one end portion of the tape being free. The panel with a coated strip attached was held in a rack such that the panel formed an angle of 178 degrees with the extended tape free end which was tensioned by application of a force of one kilogram applied as a hanging weight from the free end of the coated strip. The 178 degrees was used to negate any peel forces, thus ensuring that only shear strength forces were measured, in an attempt to more accurately determine the holding power of the tape being tested. The time elapsed for each tape example to separate from the test panel was recorded as the shear strength. All shear strength failures (if the adhesive failed at less than 10,000 minutes) reported herein were cohesive failures of the adhesive. Each test was terminated at 10,000 minutes, unless the adhesive failed at an earlier time (as noted).

Material Flow

Material Flow was determined as the temperature at which the material is sufficiently soft such that it will flow and compress to a thickness of 2 mm in an ARES parallel plate rheometer (TA Instruments, New Castle, Del.). Temperature measurements were made in 20° C. increments.

Complex Melt Viscosity

Complex melt viscosity of polymers of the present invention was obtained using an ARES rheometer (TA Instruments, New Castle, Del.) with a gap of 2.0 mm at 300° C. and a shear rate of 100 radians/second.

Refractive Index

The refractive index was measured at 633 nm using an Abbe refractometer available commercially, for example, from Fisher Instruments of Pittsburgh, Pa.

Preparation of Copolymers

Copolymers of the present invention were prepared according to the following method. A reactive oxalate ester was added to a suitable solvent. A polydimethylsiloxane diamine (PDMS diamine) was added and allowed to react until no amine was present as determined by titration. The molar ratio of the oxalate ester to the diamine was greater than 1:1. The desired hard segment diamine was then added in such a quantity to consume the majority of the remaining ester groups.

Example 1

Preparation and Characterization of Silicone Polyoxamide Using Diphenyl Oxalate in CH$_2$Cl$_2$ Solution

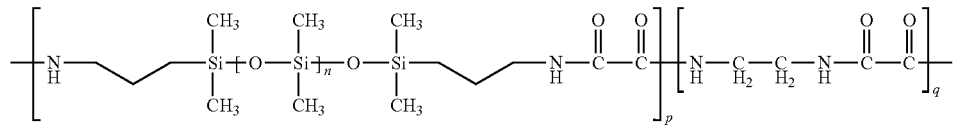

A 16 oz glass jar was charged with diphenyl oxalate (1.147 g, available from TCI America, Portland, Oreg.), CH$_2$Cl$_2$ (200 mL), and an unstripped 25 k PDMS diamine (AEW=14103 g/mol, 66.78 g, 4.735 mmol of —NH$_2$). The jar was capped and placed on a roller for 2 h. Ethylene diamine (3.00 mL of a toluene solution, 4.735 mmol of —NH$_2$) was added, and the jar was capped and placed on a roller for 5 days, at which time the highly viscous, clear solution was poured into a Teflon™ tray. The solvent was evaporated at room temperature for 48 h, then in a vacuum oven at 150° C. for 48 h. The resulting clear, tough elastomer had an IV of 2.235 dL/g (0.2 g/dL in THF, 27° C.). Quantitative $^{13}$C NMR analysis was obtained and compared to a polydiorganosiloxane polyoxamide copolymer prepared according to U.S. Pat. No. 7,501,184. $^{13}$C NMR analysis confirmed segments where q≧2.

Example 2

Preparation and Characterization of Silicone Polyoxamide Using Bis(2,2,2-trifluoroethyl)Oxalate in CH$_2$Cl$_2$ Solution

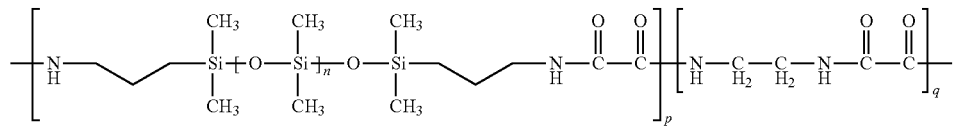

Bis(2,2,2-trifluoroethyl)oxalate was treated with the unstripped 25 k PDMS diamine and ethylene diamine according to Example 1. The resulting clear, tough elastomer had an IV of 1.494 dL/g (0.2 g/dL in THF, 27° C.).

Examples 3-19

Preparation and Characterization of Silicone Polyoxamides and Silicone Polyoxamide-Hydrazides Using Diphenyl Oxalate and Various Hard Segment Diamines in CH$_2$Cl$_2$ Solution

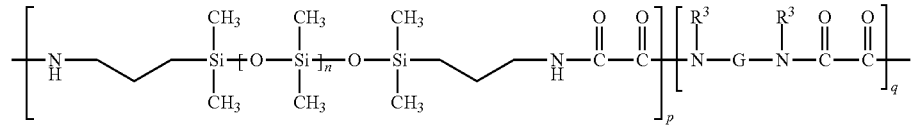

Novel silicone polyoxamides and silicone polyoxamide-hydrazides were prepared according to Example 1 using the hard segment diamines or hydrazines outlined in Table 1.

TABLE 1

| Example | Hard Segment Diamine | PDMS Diamine MW (nominal) (g/mol) | PDMS Diamine:Hard Segment Diamine (mole ratio) | IV |
|---|---|---|---|---|
| 3 | H$_2$N⌒NH$_2$ | 25 k | 1:0.5 | 2.279 |
| 4 | H$_2$N⌒NH$_2$ | 33 k | 1:1 | 2.220 |

TABLE 1-continued

| Example | Hard Segment Diamine | PDMS Diamine MW (nominal) (g/mol) | PDMS Diamine:Hard Segment Diamine (mole ratio) | IV |
|---|---|---|---|---|
| 5 | CH₃NH-CH₂CH₂-NHCH₃ | 25 k | 1:1 | 2.752 |
| 6 | H₂N-(CH₂)₃-NH₂ | 25 k | 1:1 | 2.566 |
| 7 | H₂N-(CH₂)₄-NH₂ | 25 k | 1:1 | 2.807 |
| 8 | H₂N-(CH₂)₅-NH₂ | 25 k | 1:1 | 2.769 |
| 9 | H₂N-CH₂-CH(CH₃)-(CH₂)₃-NH₂ | 25 k | 1:1 | 2.702 |
| 10 | H₂N-CH₂-CH(CH₃)-(CH₂)₃-NH₂ | 25 k | 1:0.5 | 2.544 |
| 11 | H₂N-CH₂-CH(CH₃)-(CH₂)₃-NH₂ | 33 k | 1:1 | 2.621 |
| 12 | H₂N-(CH₂)₆-NH₂ | 25 k | 1:1 | 2.831 |
| 13 | 1,3-bis(aminomethyl)benzene | 25 k | 1:1 | 2.765 |
| 14 | 1,2-diaminocyclohexane | 25 k | 1:1 | 2.621 |
| 15 | trans-1,4-diaminocyclohexane | 25 k | 1:1 | insoluble in THF |
| 16 | 4,4'-methylenebis(cyclohexylamine) | 25 k | 1:1 | 3.202 |
| 17 | piperazine | 25 k | 1:1 | 2.139 |
| 18 | 1,4-diamino piperazine | 25 k | 1:1 | 0.867 |
| 19 | H₂N-CH(CH₃)-CH₂-[O-CH₂-CH(CH₃)]ₙ-NH₂ (440 g/mol) | 25 k | 1:1 | 1.830 |

Examples 20-24

Preparation and Characterization of Silicone Polyoxamides Using Diphenyl Oxalate in Various Solvents Novel silicone polyoxamides were prepared according to Example 1 using diphenyl oxalate, the solvent indicated in Table 2, a PDMS diamine having amine equivalent weight of 12,050 g/mol, and ethylene diamine. Solubility, flow properties and melt rheology properties were determined.

TABLE 2

| Example | Solvent | Soluble in THF? | Material Flow | Complex Melt Viscosity (poise) |
|---|---|---|---|---|
| 1 | $CH_2Cl_2$ | yes | <220° C. | 2882 |
| 20 | toluene | no | 260-280° C. | 8379 |
| 21 | toluene/IPA 70/30 | no | 280-300° C. | 5916 |
| 22 | ethyl acetate | no | 240-260° C. | 9320 |
| 23 | MTBE | no | 220-240° C. | 8344 |
| 24 | MIBK | yes | 220-240° C. | 3785 |

Examples 25-35

Pressure Sensitive Adhesive Formulations from Silicone Polyoxamides

Silicone polyoxamide elastomers were prepared and isolated according to Example 1 using the PDMS diamine and hard segment diamine outlined in Table 3. The silicone polyoxamide elastomer was combined with MQ resin (Dow Corning 2-7066, 62.6% in xylenes) in THF such that the elastomer/MQ ratio was 50/50 (w/w dry solids) and the overall solids content was 25%. The solutions were knife-coated onto primed PET (HOSTAPHAN 3SAB primed polyester film available from Mitsubishi Polyester Film Inc, Greer, S.C.) at a dry thickness of about 51 μm (0.002 inches). The coated film was dried 60 minutes in a 65° C. oven. The dried film was stored overnight at 22° C. and 50% relative humidity. The resulting pressure sensitive adhesive was tested for 180° peel to glass and shear strength using the test methods outlined above.

TABLE 3

| Example | Hard Segment Diamine | PDMS Diamine MW (nominal) (g/mol) | PDMS Diamine:Hard Segment Diamine (mole ratio) | Peel Strength (N/dm) | Shear Strength (min) |
|---|---|---|---|---|---|
| 25 | $H_2N$—CH₂CH₂—$NH_2$ | 25 k | 1:1 | 78.5 | >10 k |
| 26 | $H_2N$—CH₂CH₂—$NH_2$ | 25 k | 1:0.5 | 58.7 | 1041 |
| 27 | $H_2N$—CH₂CH₂—$NH_2$ | 33 k | 1:1 | 74.0 | >10 k |
| 28 | $H_2N$—(CH₂)₄—$NH_2$ | 25 k | 1:1 | 71.4 | >10 k |
| 29 | $H_2N$—(CH₂)₅—$NH_2$ | 25 k | 1:1 | 75.8 | 2302 |
| 30 | $H_2N$—(CH₂)₆—$NH_2$ | 25 k | 1:1 | 59.6 | 6281 |
| 31 | $H_2N$—CH₂CH(CH₃)CH₂CH₂—$NH_2$ | 25 k | 1:1 | 45.6 | 424 |
| 32 | $H_2N$—CH₂CH(CH₃)CH₂CH₂CH₂—$NH_2$ | 25 k | 1:0.5 | 38.3 | 1 |
| 33 | $H_2N$—CH₂CH(CH₃)CH₂CH₂CH₂—$NH_2$ | 33 k | 1:1 | 54.5 | 127 |
| 34 | $H_2N$—(CH₂)₆—$NH_2$ | 25 k | 1:1 | 75.8 | >10 k |
| 35 | $H_2N$—CH₂—(m-C₆H₄)—CH₂—$NH_2$ | 25 k | 1:1 | 77.8 | >10 k |

Example 36

Preparation of Higher Refractive Index, Phenyl-Containing Silicone Polyoxamide

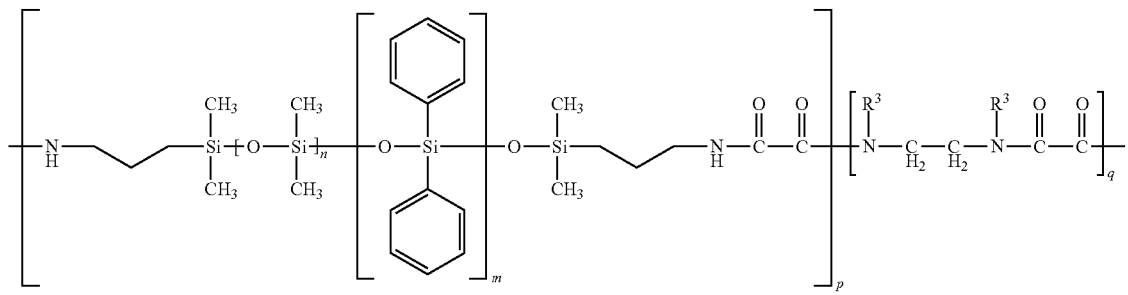

Preparation of Silicone Polyoxamide Elastomer.

An unstripped silicone diamine prepared from 90 mole percent $D_4$ and 10 mole percent octaphenyl $D_4$ was reacted with diphenyl oxalate and ethylene diamine in $CH_2Cl_2$ according to Example 1. After isolation, the resulting polymer had an IV of 2.813 dL/g (0.2 g/dL in THF, 27° C.) and a refractive index of 1.447.

Example 37

Preparation of Silicone Polyoxamide-Hydrazide Where q=1 and G is a Bond

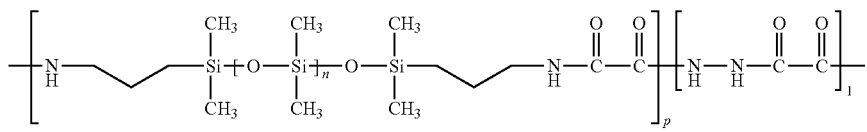

The material of the following structure, prepared according to U.S. Pat. No. 7,501,184 where Y is propylene and $R^1$ is methyl,

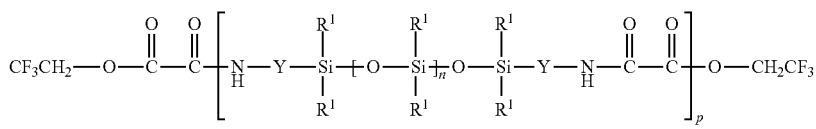

is treated with hydrazine in a molar ratio of approximately 1:1. The reaction is conducted in the presence or absence of a solvent. The elastomeric product is isolated according to the method of Example 1.

Example 38

Preparation of the Compound of Formula VI and Elastomers Therefrom

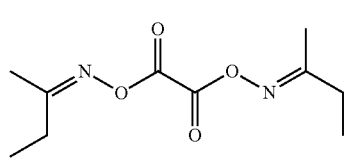

(VI)

To a 1 L flask equipped with an overhead stirrer, addition funnel, ice bath, temperature probe, and nitrogen inlet was added 2-butanone oxime (93.23 g) and MTBE (500 mL). The contents were cooled to 10° C., and oxalyl chloride (67.9 g) was added over 30 min, maintaining the internal temperature below 15° C. Triethylamine (108 g) was then added dropwise over 30 min with external cooling to maintain the internal temperature below 30° C. Enough water was added to dissolve the resulting solids, and then the aqueous layer was drawn off. The organic layer was washed twice with 0.1 N HCl and once with 2 M sodium carbonate, after which it was dried over $MgSO_4$ and filtered through a pad of CELITE. The solvent was removed on a rotary evaporator to afford 120 g of the compound of formula VI as a clear, colorless oil. $^1H$ NMR ($CDCl_3$) was consistent with the proposed structure, present as a mixture of geometrical isomers.

According to the method of Example 1, a 4 oz jar was charged with the compound of formula VI (0.343 g), THF (70.0 g), and an unstripped 25 k PDMS diamine (AEW=14, 103 g/mol, 21.25 g). The jar was placed on a roller for 1 h, and then ethylene diamine (0.754 g of a 1.982 meq/g solution in toluene) was added. The viscous material was poured into a Teflon tray and dried at 60° C. for 20 h to afford a clear, tough elastomer.

The complete disclosures of the publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. A copolymer comprising at least two repeating units of formula I:

$$\left[\begin{array}{c}R^1\\|\\-N-Y-Si+O-Si\frac{1}{n}O-Si-Y-N-C-C\\|\quad\quad|\quad\quad|\quad\quad|\quad\quad\|\quad\|\\H\quad\quad R^1\quad R^1\quad R^1\quad H\quad O\quad O\end{array}\right]_p$$
$$\left[\begin{array}{c}R^3\quad R^3\quad O\quad O\\|\quad\quad|\quad\quad\|\quad\|\\-N-G-N-C-C\end{array}\right]_q$$ (I)

wherein:
each $R^1$ is independently an alkyl, haloalkyl, aralkyl, alkenyl, aryl, or aryl substituted with an alkyl, alkoxy, or halo;
each Y is independently an alkylene, aralkylene, or a combination thereof;
each G is independently a bond or a divalent residue equal to a diamine of formula $R^3$HN-G-NH$R^3$ minus the two —NH$R^3$ groups;
each $R^3$ is independently hydrogen or alkyl or $R^3$ taken together with G and with the nitrogen to which they are both attached form a heterocyclic group;
each n is independently an integer of 0 to 1500;
each p is independently an integer of 1 to 10, and the average of p is 1.2 or greater; and
each q is independently an integer of greater than 1, and every q is not the same integer.

2. The copolymer of claim 1 wherein each $R^1$ is methyl.

3. The copolymer of claim 1 wherein each Y is an alkylene having 1 to 10 carbon atoms, phenylene bonded to an alkylene having 1 to 10 carbon atoms, or phenylene bonded to a first alkylene having 1 to 10 carbon atoms and to a second alkylene having 1 to 10 carbon atoms.

4. The copolymer of claim 1 wherein G is an alkylene, heteroalkylene, arylene, aralkylene, or a combination thereof.

5. The copolymer of claim 1 wherein G is a bond and each $R^3$ is hydrogen.

6. The copolymer of claim 1 wherein n is at least 40.

7. The copolymer of claim 1 wherein each $R^3$ is hydrogen.

8. The copolymer of claim 1 wherein the copolymer is insoluble in toluene.

9. The copolymer of claim 8 wherein the copolymer is insoluble in tetrahydrofuran.

10. The copolymer of claim 1 wherein the copolymer does not flow at or below about 220° C.

11. The copolymer of claim 10 wherein the copolymer does not flow at or below about 260° C.

12. The copolymer of claim 11 wherein the copolymer does not flow at or below about 300° C.

13. A method of making a copolymeric material comprising at least two repeat units of formula I':

$$\left[\begin{array}{c}R^1\\|\\-N-Y-Si+O-Si\frac{1}{n}O-Si-Y-N-C-C\\|\quad\quad|\quad\quad|\quad\quad|\quad\quad\|\quad\|\\H\quad\quad R^1\quad R^1\quad R^1\quad H\quad O\quad O\end{array}\right]_p$$
$$\left[\begin{array}{c}R^3\quad R^3\quad O\quad O\\|\quad\quad|\quad\quad\|\quad\|\\-N-G-N-C-C\end{array}\right]_q$$ (I')

wherein:
each $R^1$ is independently an alkyl, haloalkyl, aralkyl, alkenyl, aryl, or aryl substituted with an alkyl, alkoxy, or halo;
each Y is independently an alkylene, aralkylene, or a combination thereof;
each G is independently a bond or a divalent residue equal to a diamine of formula $R^3$HN-G-NH$R^3$ minus the two —NH$R^3$ groups;
each $R^3$ is independently hydrogen or alkyl or $R^3$ taken together with G and with the nitrogen to which they are both attached form a heterocyclic group;
each n is independently an integer of 0 to 1500;
each p is independently an integer of 1 to 10; and
each q is independently an integer of greater than 1, and every q is not the same integer;
the method comprising:
(a) adding an oxalate ester of formula II to a solvent $$R^2\text{—O—C(=O)—C(=O)—O—}R^2$$ (II)

wherein:
each $R^2$ is independently an alkyl, haloalkyl, aryl, or aryl substituted with an alkyl, alkoxy, halo, alkyoxycarbonyl, or $$\begin{array}{c}N\\\|\\R^4-C-R^4\end{array}$$

bound through the N, wherein each $R^4$ is independently hydrogen, alkyl, or aryl or $R^4$ taken together form a ring;
(b) reacting a molar excess of the oxalate ester with a polydiorganosiloxane diamine of formula III until essentially no polydiorganosiloxane diamine remains $$H_2N-Y-\underset{\underset{R^1}{|}}{\overset{\overset{R^1}{|}}{Si}}+O-\underset{\underset{R^1}{|}}{\overset{\overset{R^1}{|}}{Si}}\frac{1}{n}O-\underset{\underset{R^1}{|}}{\overset{\overset{R^1}{|}}{Si}}-Y-NH_2$$ (III)

to form the reaction product of formula IV

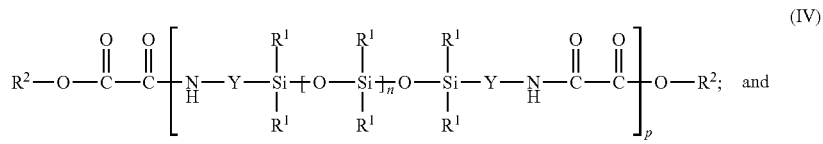

(c) adding one or more diamines of formula V to the reaction product of formula IV to form the repeat unit of formula I'

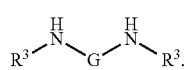

14. The method of claim 13 wherein the oxalate ester of formula II is selected from the group consisting of oxalate esters of phenol, methyl ethyl ketone oxime, acetone oxime, and trifluoroethanol.

15. The method of claim 13 wherein the solvent is selected from the group consisting of tetrahydrofuran, methyl tert-butyl ether, toluene, ethyl acetate, dichloromethane, and chloroform.

16. The method of claim 13 wherein the polydiorganosiloxane diamine of formula III has a number average molecular weight of about 1000 g/mol to about 50,000 g/mol.

17. The method of claim 13 wherein the diamine of formula V is selected from the group consisting of 1,2-diaminoethane, 1,3-diaminopropane, 1,4-diaminobutane, 1,5-diaminopentane, 2-methyl-1,5-pentanediamine, 1,6-diaminohexane, and m-xylylenediamine.

18. An article comprising the copolymer of claim 1 wherein the article is a pressure sensitive adhesive, film, mixture, or low adhesion backsize.

\* \* \* \* \*

UNITED STATES PATENT AND TRADEMARK OFFICE
CERTIFICATE OF CORRECTION

| | | |
|---|---|---|
| PATENT NO. | : 7,981,995 B2 | Page 1 of 1 |
| APPLICATION NO. | : 12/563311 | |
| DATED | : July 19, 2011 | |
| INVENTOR(S) | : David S. Hays | |

It is certified that error appears in the above-identified patent and that said Letters Patent is hereby corrected as shown below:

Column 3
Line 15, delete "alkyoxycarbonyl" and insert --alkyloxycarbonyl--

Column 5
Line 22, after "thereof" insert --.--

Column 10
Line 23, delete "alkyoxycarbonyl" and insert --alkyloxycarbonyl--

Column 14
Line 2, delete "polyoxypropylene" and insert --polyoxypropylene--

Column 15
Line 37, delete "Canon-Fenske" and insert --Cannon-Fenske--

Column 26
Line 52, delete "alkyoxycarbonyl" and insert --alkyloxycarbonyl--

Signed and Sealed this
Thirtieth Day of August, 2011

David J. Kappos
*Director of the United States Patent and Trademark Office*